US012773577B2

(12) United States Patent
Sintay et al.

(10) Patent No.: US 12,773,577 B2
(45) Date of Patent: Oct. 27, 2026

(54) SYSTEM AND METHOD TO VALIDATE AND PERFORM CODING FOR RADIATION THERAPY

(71) Applicant: The Moses H. Cone Memorial Hospital Operating Corporation, Greensboro, NC (US)

(72) Inventors: Benjamin Jeremiah Sintay, Summerfield, NC (US); Caroline Leigh Vanderstraeten, Greensboro, NC (US); David Brian Wiant, Kernersville, NC (US); Jeffrey Todd Wilson, Greensboro, NC (US)

(73) Assignee: The Moses H. Cone Memorial Hospital Operating Corporation, Greensboro, NC (US)

( * ) Notice: Subject to any disclaimer, the term of this patent is extended or adjusted under 35 U.S.C. 154(b) by 549 days.

(21) Appl. No.: 16/521,013

(22) Filed: Jul. 24, 2019

(65) Prior Publication Data

US 2020/0030635 A1 Jan. 30, 2020

Related U.S. Application Data

(60) Provisional application No. 62/702,455, filed on Jul. 24, 2018.

(51) Int. Cl.
*A61N 5/10* (2006.01)
*G06Q 30/04* (2012.01)
(Continued)

(52) U.S. Cl.
CPC ......... *A61N 5/1045* (2013.01); *A61N 5/1065* (2013.01); *G06Q 30/04* (2013.01);
(Continued)

(58) Field of Classification Search
CPC ........ G16H 10/60; G16H 15/00; G16H 10/00; G16H 70/20; G06Q 40/08; G06Q 10/10
See application file for complete search history.

(56) References Cited

U.S. PATENT DOCUMENTS 6,529,876 B1 * 3/2003 Dart ..................... G06Q 10/10 705/2
2002/0120466 A1 * 8/2002 Finn ..................... G06Q 10/10 705/2
(Continued)

FOREIGN PATENT DOCUMENTS

CA 2357415 * 3/2002
CA 2357415 A1 * 3/2002

OTHER PUBLICATIONS

C. Clinkingbeard, A. Froehlich, C. Smith, J. F. Calland and S. Guerlain, "Designing a physician's daily note template to support higher quality documentation of patient information, " 2009 Systems and Information Engineering Design Symposium, 2009, pp. 208-212, doi: 10.1109/SIEDS.2009.5166185 (Year: 2009).*

*Primary Examiner* — Joseph D Burgess
(74) *Attorney, Agent, or Firm* — Fox Rothschild LLP

(57) ABSTRACT

Systems and method for validating medical coding are provided. One such method includes detecting a recorded clinical procedure that has been performed on a patient, determining, using a processor, one or more Current Procedural Terminology (CPT) codes appropriate to the clinical procedure, and comparing the determined one or more CPT codes against one or more manually input CPT codes for the clinical procedure. The method further includes, if the determined one or more CPT codes do not match the one or more manually input CPT codes, automatically entering the determined one or more CPT codes into a medical record system.

9 Claims, 3 Drawing Sheets

(51) Int. Cl.
*G06Q 40/08* (2012.01)
*G16H 10/60* (2018.01)
*G16H 40/20* (2018.01)
*G16H 50/70* (2018.01)

(52) U.S. Cl.
CPC ............. *G06Q 40/08* (2013.01); *G16H 10/60* (2018.01); *G16H 40/20* (2018.01); *A61N 5/103* (2013.01); *G16H 50/70* (2018.01)

(56) References Cited

U.S. PATENT DOCUMENTS

| | | | | |
|---|---|---|---|---|
| 2003/0083903 | A1* | 5/2003 | Myers | G16H 15/00 705/2 |
| 2003/0154085 | A1* | 8/2003 | Kelley | G06F 40/174 704/E15.045 |
| 2005/0137910 | A1* | 6/2005 | Rao | G16H 10/60 705/3 |
| 2005/0234740 | A1* | 10/2005 | Krishnan | G16H 50/70 705/7.42 |
| 2013/0151265 | A1* | 6/2013 | Kos | G16H 20/40 705/2 |
| 2014/0019160 | A1* | 1/2014 | Loya, III | G16H 15/00 705/3 |
| 2016/0012187 | A1* | 1/2016 | Zasowski | G16H 40/67 705/3 |
| 2016/0203279 | A1* | 7/2016 | Srinivas | G16H 10/60 705/2 |
| 2017/0068781 | A1* | 3/2017 | Zasowski | G16H 10/60 |

* cited by examiner

SYSTEM AND METHOD TO VALIDATE AND PERFORM CODING FOR RADIATION THERAPY

TECHNICAL FIELD

The present disclosure relates to medical coding and, more specifically, to the coding complexities of radiation therapy.

BACKGROUND

Radiation therapy is the practice of delivering high energy radiation for therapeutic medical purposes and, primarily, to reduce or eliminate cancerous tissues or provide treatment for other non-cancerous diseases. Radiation can be delivered either externally, often referenced as external beam radiation therapy (EBRT), or internally, through a process called "brachytherapy". For either external or internal radiation therapy, the method of generating and delivering radiation can vary greatly. There is a corresponding difference in the level of effort and complexity imposed on the medical team, as well as the technology required, to produce a treatment.

Radiation therapy often requires the use of billing codes. The primary use of billing codes is to translate the level of effort and specific activities performed into discrete units of measure for the purpose of communicating those activities and their associated costs to payors. Payors may include third-party insurance companies, government entities, or private citizens. Secondarily, billing codes are frequently used internally by healthcare corporations to track statistics for budgeting, productivity, and benchmarking of labor and resources.

The process billing and coding of radiation therapy treatments, medical devices, and services is a highly complex process. Billing depends on a number of factors, including what specific tasks have been performed, the number of tasks, and the time and labor intensity of the tasks. Adding to the complexity is the idea of "families of billing codes" or "billing code families." Billing code families must be billed together to be valid. In many cases, the prior history of the patient must be examined to determine how to bill a new procedure. Finally, there must be clinical evidence and documented activities to support the specific codes used for a given patient.

The current processes includes manually capturing charges and validating their accuracy. This is performed by medical professionals during the process of delivering healthcare and by internal auditors after billing codes are generated and saved in the electronic medical record database. The sheer number of charges and the complexity of the coding system make it very difficult and time consuming to manually enter and validate charges. This time consumption and level of difficulty increase the costs associated with billing and coding. There is thus presently a need for a system and method to perform this work quickly while reducing human error.

If activities or services are performed without the generation of billing codes, healthcare corporations stand to lose a significant amount of income. Additionally, if codes are generated without proper evidence to support them, this 1) unnecessarily raises the cost of healthcare to the consumer, and 2) puts those healthcare income at risk for recovery due to an audit (either internal or external) or payor investigation. In the end, it is the desire of both the payors and healthcare corporations for charges to accurately reflect the work performed, and for the proper documentation to be present to support the particular billing codes.

SUMMARY

According to an aspect of the present disclosure, a method for validating medical coding is provided. The method includes detecting a recorded clinical procedure that has been performed on a patient, determining, using a processor, one or more Current Procedural Terminology (CPT) codes appropriate to the clinical procedure, and comparing the determined one or more CPT codes against one or more manually input CPT codes for the clinical procedure. The method further includes, if the determined one or more CPT codes do not match the one or more manually input CPT codes, automatically entering the determined one or more CPT codes into a medical record system.

It is an object of the present disclosure to provide the method for validating medical coding, wherein the clinical procedure is a radiation therapy procedure.

It is an object of the present disclosure to provide the method for validating medical coding, wherein the clinical procedure is a clinical procedure that requires billing, and wherein the detecting a clinical procedure that has been performed on the patient further includes determining whether a clinical procedure requires billing.

It is an object of the present disclosure to provide the method for validating medical coding, wherein the method further includes determining whether the clinical procedure is appropriately documented.

It is an object of the present disclosure to provide the method for validating medical coding, wherein, if it is determined that the clinical procedure is not appropriately documented, notifying one or more end-users.

It is an object of the present disclosure to provide the method for validating medical coding, wherein the notification includes information pertaining to the clinical procedure.

It is an object of the present disclosure to provide the method for validating medical coding, wherein the information pertaining to the procedure is selected from the group consisting of: patient name; date of the clinical procedure; and type of the clinical procedure.

It is an object of the present disclosure to provide the method for validating medical coding, wherein the method further includes, if the determined one or more CPT codes do not match the one or more manually input CPT codes, notifying an end-user that the determined one or more CPT codes do not match the one or more manually input CPT codes.

It is an object of the present disclosure to provide the method for validating medical coding, wherein the notification includes information pertaining to the clinical procedure.

It is an object of the present disclosure to provide the method for validating medical coding, wherein the information pertaining to the procedure is selected from the group consisting of: patient name; date of the clinical procedure; and type of the clinical procedure.

It is an object of the present disclosure to provide the method for validating medical coding, wherein the method further includes, if the determined one or more CPT codes do not match the one or more manually input CPT codes, automatically, using the processor, generating one or more CPT codes.

It is an object of the present disclosure to provide the method for validating medical coding, wherein the method further includes, if the determined one or more CPT codes match the one or more manually input CPT codes, marking the one or more manually input CPT codes as reviewed.

According to another aspect of the present invention, a system for validating medical coding is provided. The system includes a billing validation and creation system that includes a transceiver configured to access one or more databases and to receive information from the one or more databases, a memory configured to store information sent from the one or more databases, and graphical user interface. The billing validation and creation system further includes a processor configured to detect a recorded clinical procedure that has been performed on a patient, determine one or more Current Procedural Terminology (CPT) codes appropriate to the clinical procedure, compare the determined one or more CPT codes against one or more manually input CPT codes for the clinical procedure, and, if the determined one or more CPT codes do not match the one or more manually input CPT codes, automatically enter the determined one or more CPT codes into a medical record system.

It is an object of the present disclosure to provide the system for validating medical coding, wherein the clinical procedure is a radiation therapy procedure.

It is an object of the present disclosure to provide the system for validating medical coding, wherein the processor is further configured to determine whether the clinical procedure is appropriately documented, and wherein, if it is determined that the clinical procedure is not appropriately documented, the processor is further configured to send a notification to one or more end-users, using the transceiver.

It is an object of the present disclosure to provide the system for validating medical coding, wherein, if the determined one or more CPT codes do not match the one or more manually input CPT codes, the processor is further configured to notify, using the transceiver, an end-user that the determined one or more CPT codes do not match the one or more manually input CPT codes.

It is an object of the present disclosure to provide the system for validating medical coding, wherein the notification includes information pertaining to the clinical procedure.

It is an object of the present disclosure to provide the system for validating medical coding, wherein the information pertaining to the procedure is selected from the group consisting of: patient name; date of the clinical procedure; and type of the clinical procedure.

It is an object of the present disclosure to provide the system for validating medical coding, wherein, if the determined one or more CPT codes do not match the one or more manually input CPT codes, automatically, the processor is further configured to generate one or more CPT codes.

It is an object of the present disclosure to provide the system for validating medical coding, wherein, if the determined one or more CPT codes match the one or more manually input CPT codes, the processor is further configured to mark as reviewed the one or more manually input CPT codes.

DETAILED DESCRIPTION

Figure 1:
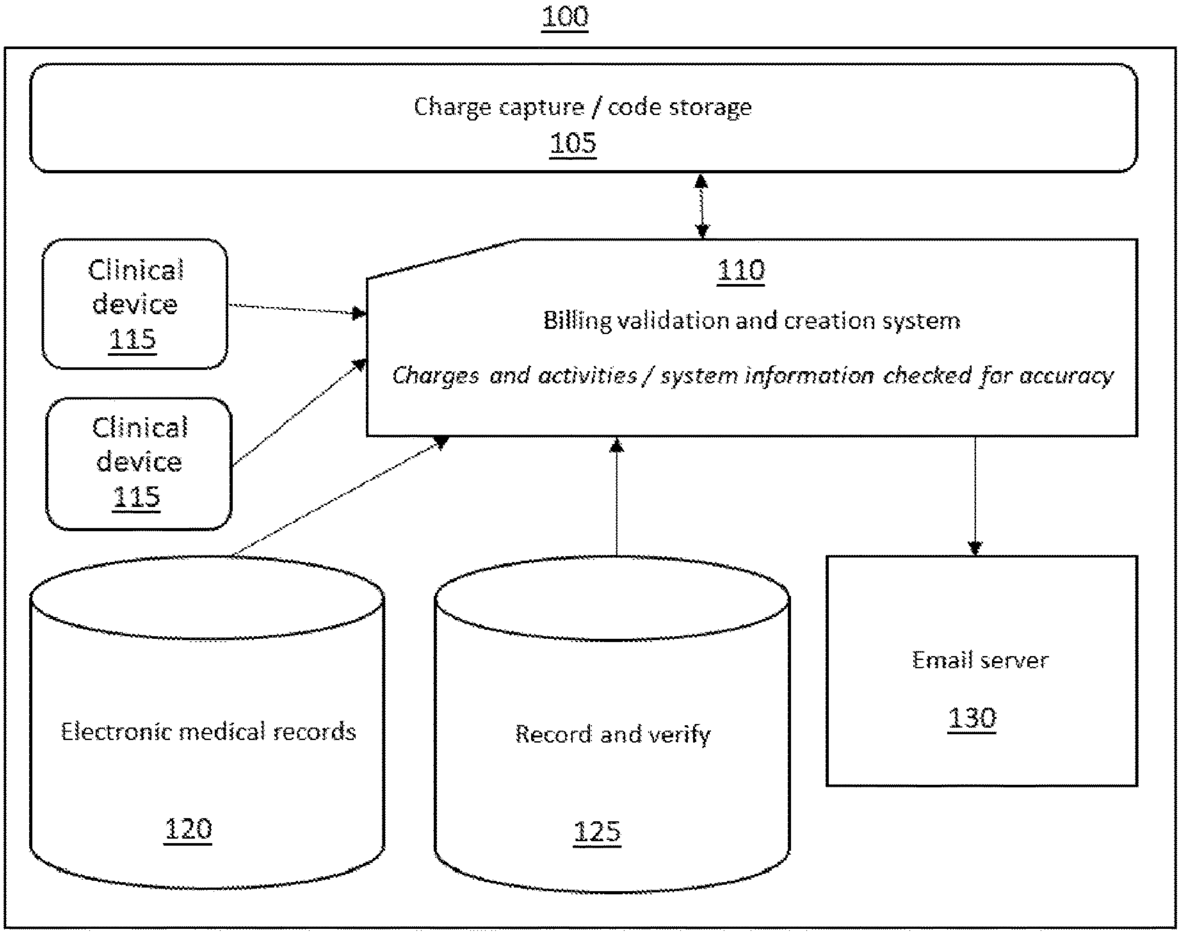
FIG. 1 is block diagram of an example of a system of the present disclosure for validating and automatically creating charge codes for medical billing.

Some implementations of the present disclosure will now be described more fully hereinafter with reference to the accompanying drawings, in which some, but not all implementations of the disclosure are shown. Indeed, various implementations of the disclosure may be embodied in many different forms and should not be construed as limited to the implementations set forth herein; rather, these example implementations are provided so that this disclosure will be thorough and complete, and will fully convey the scope of the disclosure to those skilled in the art.

As used in this document, the singular forms "a," "an," and "the" include plural references unless the context clearly dictates otherwise. Unless defined otherwise, all technical and scientific terms used herein have the same meanings as commonly understood by one of ordinary skill in the art. As used in this document, the term "comprising" (or "comprises") means "including (or includes), but not limited to." When used in this document, the term "exemplary" is intended to mean "by way of example" and is not intended to indicate that a particular exemplary item is preferred or required.

In this document, when terms such "first" and "second" are used to modify a noun, such use is simply intended to distinguish one item from another, and is not intended to require a sequential order unless specifically stated. The term "approximately," when used in connection with a numeric value, is intended to include values that are close to, but not exactly, the number. For example, in some embodiments, the term "approximately" may include values that are within +/−10 percent of the value.

An "electronic device" or a "computing device" refers to a device or system that includes a processor and memory. Each device may have its own processor and/or memory, or the processor and/or memory may be shared with other devices as in a virtual machine or container arrangement. The memory will contain or receive programming instructions that, when executed by the processor, cause the electronic device to perform one or more operations according to the programming instructions. Examples of electronic devices include personal computers, servers, mainframes, virtual machines, containers, gaming systems, televisions, digital home assistants and mobile electronic devices such as smartphones, Internet-connected wearables such as smart watches and smart eyewear, personal digital assistants, cameras, tablet computers, laptop computers, media players and the like. Electronic devices also may include equipment and other devices that can communicate in an Internet-of-things arrangement. In a client-server arrangement, the client device and the server are electronic devices, in which the server contains instructions and/or data that the client device accesses via one or more communications links in one or more communications networks. In a virtual machine arrangement, a server may be an electronic device, and each virtual machine or container also may be considered an electronic device. In the discussion below, a client device, server device, virtual machine or container may be referred to simply as a "device" for brevity. Additional elements that may be included in electronic devices will be discussed below.

The terms "processor" and "processing device" refer to a hardware component of an electronic device that is configured to execute programming instructions. Except where specifically stated otherwise, the singular terms "processor" and "processing device" are intended to include both single-processing device embodiments and embodiments in which multiple processing devices together or collectively perform a process.

The terms "memory," "memory device," "data store," "data storage facility" and the like each refer to a non-transitory device on which computer-readable data, programming instructions or both are stored. Except where specifically stated otherwise, the terms "memory," "memory device," "data store," "data storage facility" and the like are intended to include single device embodiments, embodiments in which multiple memory devices together or collectively store a set of data or instructions, as well as individual sectors within such devices.

In this document, the terms "communication link" and "communication path" mean a wired or wireless path via which a first device sends communication signals to and/or receives communication signals from one or more other devices. Devices are "communicatively connected" if the devices are able to send and/or receive data via a communication link. "Electronic communication" refers to the transmission of data via one or more signals between two or more electronic devices, whether through a wired or wireless network, and whether directly or indirectly via one or more intermediary devices.

Referring now to FIG. 1, a system 100 for validating and automatically creating charge codes for medical billing is illustratively depicted in accordance with an embodiment of the present disclosure.

Medical billing codes are sometimes referred to as Current Procedural Terminology (CPT) codes, and are a listing of medical codes that are used to report medical, surgical, and diagnostic procedures and services to entities such as physicians, health insurance companies and accreditation organizations. The billing codes are patient-specific and require particular quantity and selection based on clinical activities. Because of this, the accuracy of the billing codes, for patient safety and for billing purposes, is paramount.

Determining billing codes requires an accurate understanding and knowledge of a patient's medical records, since not all procedures incorporate the same codes every time that the procedures are performed. Some codes have specific modifiers that change based on additional documentation, circumstances, or procedures. Therefore, multiple factors concerning a procedure and the patient can be identified by the billing codes.

The current state of the art requires a significant amount of human interaction in performing assigning billing codes and in determining the accuracy of billing codes. For example, medical and billing professionals often access and manipulate healthcare information and billing data on a server from their personal electronic devices. Treatment charges are often manually entered into a medical record/billing system at the completion of each procedure by the technologist and/or medical provider delivering the procedure. These charges are typically given a cursory review at the end of each day by a technologist for 1-2 hours. At the end of each patient billing cycle, a billing/coding specialist reviews a patient's charges for accuracy. At some places an additional layer of spot checking may occur. Each of these human interactions increases the time and cost of billing and increases the risk of human error.

The present disclosure, however, provides a system 100 and method 200 that significantly reduces the amount of human interaction required by using server hardware to execute specific services that perform the coding functions. The results of these actions can be viewed through reports, specific communications such as automatic emails, and through a system interface that displays information regarding coding correctness. By reducing the human interactions required to perform these functions, the systems and methods of the present disclosure reduce the timeframe needed to perform these functions and reduce the costs associated with these functions, thus improving upon the existing technologies in the art. Additionally, the system 100 and method 200 of the present disclosure uses automation to decrease common errors made in this field. Incorrect billing likely results in charges being denied by payors. These unpaid bills can amount to large sums of uncompensated care, into the millions of dollars for a medium or large radiation oncology center.

Radiation therapy billing codes are often stored in a shared database 120 with electronic medical records. Patients using radiation therapy may require various numbers of radiation activities and/or one or more different type of radiation therapy treatment. Taking this into account, radiation therapy CPT codes are based on the number and type of procedures that are performed. Third party payors (e.g., third-party insurance companies, government entities, private citizens, etc.) typically require each specific procedure to be supported or proven by discrete pieces of information. Therefore, if a radiation therapy provider accurately documents the performance of each procedure, there should be discrete data that accurately represents each CPT code that should be billed. This helps insure the accuracy of the procedures both performed and billed.

In current radiation therapy practice, nearly all of this discrete data is stored electronically in clinical devices 115, electronic medical records storage 120, record and verify systems 125, and/or other databases that are accessible to the treatment provider. Some examples of discrete data that support clinical procedures include, but are not limited to, the radiation prescription prepared by the medical professional, any physician orders, clinical documentation, notes, planning and delivery techniques, diagnosis codes, medications, equipment used, imaging methods, time spent, quantity of certain items, complexity of activities, and modality.

It is noted that, while examples presented herein may be focused on clinical procedures providing radiation therapy, the present system 100 and method 200 may be applied to any suitable form of clinical procedure.

According to an embodiment, this discrete digital data is stored on one or more systems that can be accessed via a computer network or other digital data source. Examples of these systems may include, e.g., one or more databases 120 configured to store captured charges and/or billing codes, one or more clinical devices 115, one or more databases 120 configured to store medical records, one or more recording and verify systems 125 configured to log one or more activities of therapy machines and treatment plans, the treatment planning systems, contouring systems used to define the location of various anatomic regions of interest, one or more email and/or other electronic communication servers 130, and/or any other suitable clinical devices and/or databases. According to an embodiment, one or more of the components of system 100 may be coupled to one or more other components of system 100 via one or more communication paths.

According to an embodiment, the activities of interest can be cataloged along with any relevant approvals or sign-offs, dates and times, complexity of the activity, and/or any other relevant information. These data points are used as the basis for supporting billing codes, either to generate new codes from the activities as a part of the coding features, or to validate existing codes against activities and documentation. The execution of this system 100 yields timely and accurate billing codes, thereby reducing complexity and effort by personnel. The present disclosure thereby improves coding for clinical procedures by providing a novel system 100 and method 200 to validate billing codes against clinical evidence as well as automatically bill based on data in the medical record and/or other databases.

According to an embodiment, the system 100 may run automatically on a set schedule, continuously by short periodic polling, and/or on-demand to extract information from the medical and billing record stored in one or more databases 105, 120.

According to an embodiment, the system 100 includes a billing validation and creation system 110. The billing validation and creation system 110 may include one or more processors, storage media, graphical user interfaces, and/or any other suitable components for performing billing validation. According to an embodiment, the billing validation and creation system 110 is configured to perform a validation feature. According to an embodiment, the billing validation and creation system is initially configured by an end-user. The end-user may be a health system, a health or other relevant department, a Centers for Medicare & Medicaid Services (CMS) regional office (or office of one or more similar agencies), and/or any other suitable end-user.

The validation feature of the system 110 compares data from the medical and billing record to one or more coding standards, documentation requirements, and/or code families or interdependencies in order to determine the correct codes or activities required for a particular procedure for a particular patient. According to an embodiment, the system 110 determines, based on the comparison, any mismatches, errors, and/or omissions in the registered billing codes for the particular patients for the particular procedures. According to an embodiment, any mismatches, errors, and/or omissions are flagged and may be shown through a graphical user interface 113 or sent as a message to healthcare personnel through the digital communication server 130.

According to an embodiment, system 110 is further configured to generate and/or suggest one or more billing codes automatically based on certain criteria and/or data points. According to an embodiment, the system 110 searches for one or more clinical activities, specific parameters of the treatment plan, execution records from diagnostic and treatment machines, record and verify systems, orders, and/or documentation, and generates an appropriate billing code to capture, sending the generated billing code into the electronic medical record data storage 120 and billing system 105 automatically.

Figure 2:
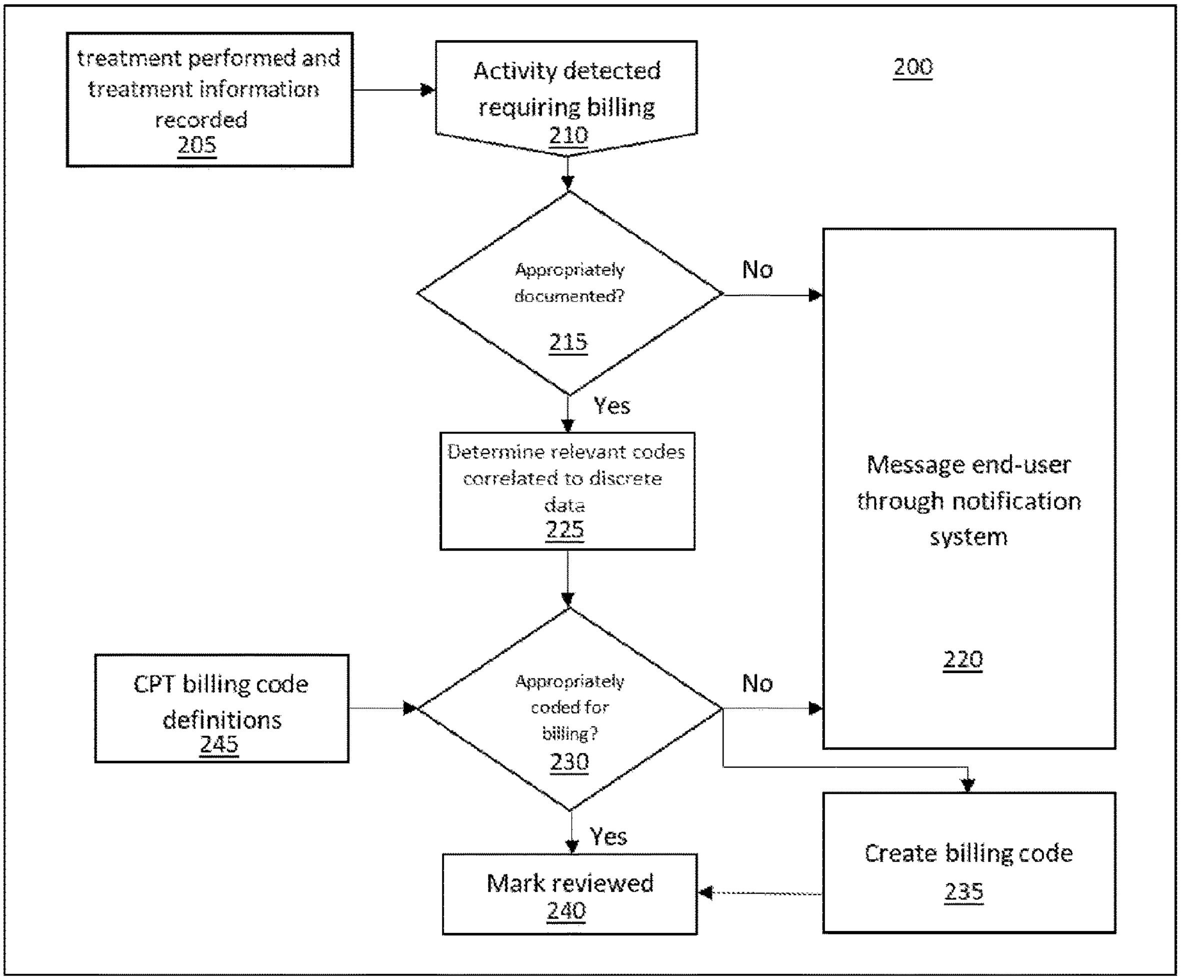
FIG. 2 is a flowchart of an example of a method of the present disclosure for validating and automatically creating charge codes for medical billing.

Referring now to FIG. 2, a method 200 for validating and automatically creating charge codes for medical billing is illustratively depicted in accordance with an embodiment of the present disclosure.

According to an embodiment, a clinical procedure is performed on a patient and the clinical activity delivery device records the clinical activity information 205. According to an embodiment, the clinical procedure may be a treatment procedure and/or any other form of clinical action and/or activity that recorded. According to an embodiment, the clinical procedure may be, but is not limited to, a radiation treatment procedure. It is noted, however, that method 200 may be implemented in any suitable type of clinical procedure and not merely for radiation treatment procedures. Once the clinical procedure is completed, the billing validation and creation system detects this activity 210 as an activity that requires billing.

According to an embodiment, once the activity has been detected by the billing validation and creation system, the billing validation and creation system determines 215 if the activity has been appropriately documented with all necessary information required for that activity. According to various embodiments, in order to determine whether treatment has been appropriately documented, the billing validation and creation system searches the available databases for all treatment related discrete data from the current day and any prior data needed to verify charge families and validates that this data has appropriate approvals. According to an embodiment, if the billing validation and creation system determines that the treatment was not appropriately documented, the billing validation and creation system notifies, at 220, one or more end-users, using the digital communications server, that the treatment has not been appropriately documented and requests that updated treatment documentation be supplied.

According to an embodiment, the billing validation and creation system determines which CPT codes are correlated to the discrete data pertaining to the treatment, based on data collected at 215. The billing validation and creation system may retrieve CPT billing code definitions at 245 from one of more storage units housing the information in order to determine which CPT codes are correlated to the discrete data. According to an embodiment, the billing validation and creation system identifies the different billable events that may occur at a user's site. Examples of billable events include, but are not limited to, complex treatments, complex treatments plus interfraction localization, simple treatments, intensity-modulated radiation therapy (IMRT) treatments, 3D plans, IMRT plans, complex isodose plans, etc. According to an embodiment, each of these events 1) must be supported by specific pieces of discrete electronic information available in either the medical record system or the oncology information system and 2) allows for specific CPT codes to be billed. According to an embodiment, once the different billable events that may occur are identified, the billing validation and creation system matches the billable events to a list of discrete elements that support it and to a list of CPT codes that may be billed.

The billing validation and creation system then compares the predicted CPT codes to any that have been manually entered into the hospital medical record system to determine if the treatment has been appropriately coded, at 230.

If it is determined that the treatment has not been appropriately coded, the billing validation and creation system, at 220, messages one or more end-users, using the digital communications server, to notify the one or more end-users that the entered billing code or codes for the treatment are not appropriate for the treatment. According to an embodiment, the billing validation and creation system reaches out to an administrator by email, through a software interface, text message alert, a notification pushed to a listening device such as a smartphone, a process contained within the notification system, and/or through any other suitable means of communication. According to an embodiment, the notification may include information pertaining to the procedure, such as the patient name, date of procedure, type of procedure, and/or any other relevant information. Furthermore, the billing validation and creation system may, at 235, enter the generated CPT codes that correlate with the treatment, and which were determined at 225, into the hospital medical record system.

If it is determined that the treatment has been appropriately coded, the billing validation and creation system, at 240, the record is marked as reviewed in the billing validation and creation system's database.

According to an embodiment, the billing validation and creation system is run at discrete time intervals or on demand. According to an embodiment, if the billing validation and creation system is run daily, it determines which patients had clinical activity on a particular day (i.e. patients that received a treatment or had a treatment plan approved by a physician). The billing validation and creation system then analyzes each patient that had clinical activity and checks the databases for any discrete data that could be associated with the clinical activity and any CPT codes associated with the patient for that day. Next, the billing validation and creation system tries to match the recently found discrete data to a list of specific pieces of discrete electronic information and a list of CPT codes that may be billed. If the billing validation and creation system finds a match from the lists it then checks to see if the current active CPT codes match what is stored in the system. Any events that do not find a match in the list get flagged for missing documentation. Any disagreements between predicted CPT codes and matched CPT codes gets reported with the suggested CPT codes.

The automatic handling of billing code families is an important feature of the present system 100 and method 200. Billing code families arise from codes that are interdependent on one another, often originating at different points in time. When manually billing (or manually auditing charge codes) it is difficult and time consuming to look back and find previous codes or activities and determine how they affect current charges. For example, some activities and associated billing codes for preparing a plan for clinical procedures have corresponding clinical activity delivery codes. Failure to correctly identify and match these codes could lead to revenue loss or overbilling. The system 100 and method 200 are configured to store these code families in an adjustable database that can easily be referenced during execution to ensure accurate billing.

A clear duality emerges from the need to use both billing codes and clinical data to correctly bill patients. Both are checked against each other for completeness and familial abnormalities. Information is presented to users, at 220, for correction if the correction cannot be completed automatically. Finally, clinical documentation and activities may change over time, thus modifying the documented support for a given billing code. According to an embodiment, the billing validation and creation system 110 can be run at any time to re-validate previous billing codes with their corresponding documentation and discrete activity data points. According to an embodiment, this can be executed in multiple ways including, but not limited to, on a per patient basis, by billing code, by healthcare provider, and/or by date range.

Figure 3:
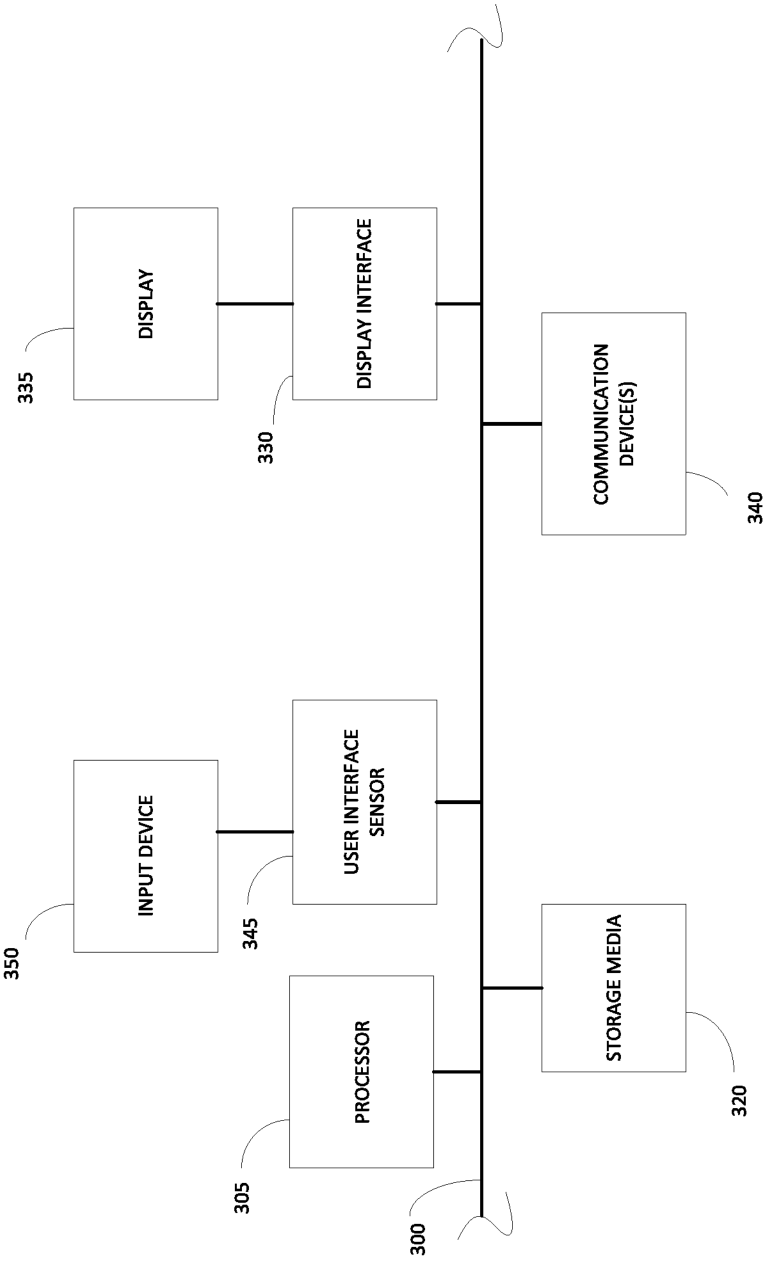
FIG. 3 is a block diagram of a computer system in accordance with the present disclosure.

Referring now to FIG. 3, an example of internal hardware that may be included in any of the electronic components of the system 100, such as clinical devices 115 and one or more components of the billing validation and creation system 110, is depicted. An electrical bus 300 serves as an information highway interconnecting the other illustrated components of the hardware. Processor 305 is a central processing device of the system, configured to perform calculations and logic operations required to execute programming instructions. As used in this document and in the claims, the terms "processor" and "processing device" may refer to a single processor or any number of processors in a set of processors that collectively perform a set of operations, such as a central processing unit (CPU), a graphics processing unit (GPU), a remote server, or a combination of these. Read only memory (ROM), random access memory (RAM), flash memory, hard drives and other devices capable of storing electronic data constitute examples of memory devices 325. A memory device may include a single device or a collection of devices across which data and/or instructions are stored.

An optional display interface 330 may permit information from the bus 300 to be displayed on a display device 335 in visual, graphic or alphanumeric format. An audio interface and audio output (such as a speaker) also may be provided. Communication with external devices may occur using various communication devices 340 such as a wireless antenna, an RFID tag and/or short-range or near-field communication transceiver, each of which may optionally communicatively connect with other components of the device via one or more communication system. The communication device 340 may be configured to be communicatively connected to a communications network, such as the Internet, a local area network or a cellular telephone data network.

The hardware may also include a user interface sensor 345 that allows for receipt of data from input devices 350 such as a keyboard, a mouse, a joystick, a touchscreen, a touch pad, a remote control, a pointing device and/or microphone.

While certain embodiments of the invention have been described using specific terms, such description is for present illustrative purposes only, and it is to be understood that changes and variations to such embodiments, including but not limited to the substitution of equivalent features or parts, and the reversal of various features thereof, may be practiced by those of ordinary skill in the art without departing from the spirit or scope of the present disclosure. For example, the present system 100 is not limited to use with radiology procedures. Rather, the system 100 may also be easily adapted for use with other types of clinical procedures that result in the use of CPT codes.

The invention claimed is:

1. A method for validating medical coding, comprising:

correlating specific pieces of discrete electronic information that validate a clinical treatment procedure was performed and storing, by one or more processors, corresponding Current Procedural Terminology (CPT) codes;

providing clinical procedure delivery devices, electronic medical records storage, and record and verify system, which are connected over a communication network of a treatment facility;

generating, by one or more processors, discrete data from conducting imaging, treatment, planning, and examinations procedures at the treatment facility;

storing the generated discrete data in associated clinical procedure delivery devices, electronic medical records storage, and record and verify system, wherein the discrete data includes radiation prescriptions prepared by a medical professional, physician orders, clinical documentation, notes, planning and delivery techniques, diagnosis codes, medications, equipment used, imaging methods, and modality;

performing a clinical procedure on patients using the clinical procedure delivery devices that apply a medical treatment to patients;

automatically detecting, by one or more processors, which patients had clinical activity at the treatment facility on a particular day;

on a set schedule, automatically, by one or more processors, searching the clinical procedure delivery devices, electronic medical records storage, and record and verify system to find, for the detected patients, the specific pieces of electronic information that validate that a corresponding procedure was performed, and and collecting the search results;

automatically determining, by one or more processors, that a treatment performed on the patient was omitted from a detected patient's medical record, by matching the search results to the specific pieces of discrete electronic information that validate that the clinical treatment procedure was performed on the patient and using the matching to correlate discrete data to a medical treatment having a corresponding one of the CPT codes and CPT code families;

displaying information on a graphical user interface regarding the CPT code;

automatically entering, by one or more processors, the determined one or more CPT codes into the patient specific medical record system; and using, by one or more processors, the determined one or more CPT codes for generating an accurate patient specific bill based on the detected clinical procedure.

2. The method as recited in claim 1, wherein the clinical procedure is a radiation therapy procedure.

3. The method as recited in claim 1, wherein the clinical procedure is a clinical procedure that requires billing, and wherein the detecting the clinical procedure that has been performed on the patient further includes determining whether a clinical procedure requires billing.

4. The method as recited in claim 1, further comprising:

when the determined one or more CPT codes do not match one or more manually input CPT codes, automatically, using the determined one or more CPT codes.

5. A system for validating medical coding, comprising:

Clinical procedure delivery devices, electronic medical records storage, and record and verify system, which are connected over a communication network of a treatment facility, and which generate discrete data from conducting imaging, treatment, planning, and examination procedures at the treatment facility;

clinical procedure delivery devices configured to apply a medical treatment to patients;

a billing validation and creation system, including:

a transceiver configured to access databases of clinical procedure delivery devices, electronic medical records storage, and record and verify system and to receive information from the databases;

a memory, configured to store information sent from databases, and store correlation of specific pieces of discrete electronic information that that validate a clinical treatment procedure was performed with corresponding Current Procedural Terminology (CPT) codes, and store the generated discrete data in associated clinical procedure delivery devices, electronic medical records storage, and record and verify system, wherein the discrete data includes radiation prescriptions prepared by a medical professional, physician orders, clinical documentation, notes, planning and delivery techniques, diagnosis codes, medications, equipment used, imaging methods, and modality;

a graphical user interface; and a processor, configured to:

automatically detect which patients had clinical activity at the treatment facility on a particular day;

on a set schedule, automatically search the databases to find, for the detected patients, the specific pieces of electronic information that validate that a corresponding procedure was performed, and collect the search results;

automatically determine that a treatment performed on the patient was omitted from a detected patient's medical record, by matching the search results to the specific pieces of discrete electronic information that validate that the clinical treatment procedure was performed on the patient and using the matching to correlate discrete data to a medical treatment having a corresponding one of the CPT codes and CPT code families;

display information on the graphical user interface regarding the CPT code; and automatically enter the determined one or more CPT codes into the patient specific medical record system, and use the determined one or more CPT codes for generating an accurate patient specific bill based on the detected clinical procedure.

6. The system as recited in claim 5, wherein the clinical procedure is a radiation therapy procedure.

7. The system as recited in claim 5, wherein, when the determined one or more CPT codes do not match one or more manually input CPT codes, the processor is further configured to automatically use the one or more CPT codes.

8. The system as recited in claim 5, wherein, when the determined one or more CPT codes match the one or more pre-registered CPT codes, the processor is further configured to mark as reviewed the one or more pre-registered CPT codes.

9. The method as recited in claim 1, further comprising repeating the steps of claim 1 upon occurrence of an event, the event comprising at least one of the following: expiration of a threshold time period, periodic polling event, or a request for a bill for the clinical procedure.

* * * * *